US007776361B2

(12) United States Patent
Ting

(10) Patent No.: US 7,776,361 B2
(45) Date of Patent: Aug. 17, 2010

(54) NELL-1 ENHANCED BONE MINERALIZATION

(75) Inventor: Kang Ting, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/392,294

(22) Filed: Mar. 28, 2006

(65) Prior Publication Data

US 2006/0228392 A1    Oct. 12, 2006

Related U.S. Application Data

(63) Continuation of application No. 09/412,297, filed on Oct. 5, 1999, now Pat. No. 7,052,856.

(51) Int. Cl.
*A61K 35/32* (2006.01)
*A61K 51/00* (2006.01)
*A61K 35/12* (2006.01)
*A61K 38/00* (2006.01)
*A61B 5/055* (2006.01)

(52) U.S. Cl. ............... 424/549; 424/1.25; 424/9.322; 424/520; 530/300

(58) Field of Classification Search ............. 424/1.25, 424/1.33, 9.323, 423, 426, 444; 530/300
See application file for complete search history.

(56) References Cited

U.S. PATENT DOCUMENTS

| 4,394,370 | A | * | 7/1983 | Jefferies ............... 606/76 |
| 4,409,332 | A | | 10/1983 | Jefferies et al. |
| 5,385,887 | A | | 1/1995 | Yim et al. |
| 5,486,359 | A | | 1/1996 | Caplan et al. |
| 5,674,725 | A | | 10/1997 | Beertsen et al. |
| 5,674,844 | A | | 10/1997 | Kuberasampath et al. |
| 5,763,416 | A | * | 6/1998 | Bonadio et al. ........ 514/44 R |
| 5,854,207 | A | | 12/1998 | Lee et al. |
| 5,916,870 | A | | 6/1999 | Lee et al. |
| 5,942,496 | A | | 8/1999 | Bonadio et al. |
| 5,948,428 | A | | 9/1999 | Lee et al. |
| 6,077,987 | A | * | 6/2000 | Breitbart et al. ........ 623/23.72 |
| 6,083,690 | A | | 7/2000 | Harris et al. |
| 6,200,606 | B1 | | 3/2001 | Peterson et al. |
| 6,352,972 | B1 | | 3/2002 | Nimni et al. |
| 6,413,998 | B1 | | 7/2002 | Petrie et al. |
| 6,462,019 | B1 | | 10/2002 | Mundy et al. |
| 2003/0143688 | A1 | | 7/2003 | Fujiwara et al. |
| 2006/0053503 | A1 | | 3/2006 | Culiat et al. |

FOREIGN PATENT DOCUMENTS

WO    WO 01/24821    4/2001
WO    WO 2004/024893    3/2004

OTHER PUBLICATIONS

Ting et al, 1999, (Journal of Bone Mineral Research, 14;80-89).*
Watanabe et al, 1996, (Genomics 38(3):273-276).*
Bowie et al (Science, 1990, 257:1306-1310).*
Greenspan et al. (Nature Biotechnology 7: 936-937, 1999).*
Ting et al (Journal of Bone and Mineral Research, vol. 14, No. 1, 1999).*
Beck et al. (1991) "Rapid Publication TGF-$\beta_1$ Induces Bone Closure of Skull Defects." *Bone Miner. Res.* 11:1257-1265.
Bellows, C.G. et al. "Determination of Numbers of Osteoprogenitors Present in Isolated Fetal Rat Calvaria Cells in Vitro." Dev. Biol. (1989) 133(1), pp. 8-13.
Burger, E.H. et al., "Osteoblast and Osteoclast Precursors in Primary Cultures of Calvarial Bone Cells." Anat Rec. Jan. 1986; 214(1): 32-40. Abstract only.
Chen et al. (1998) "Structure, Chromosomal Localization, and Expression Pattern of the Murine *Magpo* Gene," *Biol Chem.* 168:17381-27389.
Crawford et al. (1998) "Thrombospondin-1 is a Major Activator of TGF-$\beta_1$ in Vivo." *Cell* 93(7):1159-1170.
Francois and Bier (1995) "*Zenopus chordin* and *Drosophilia short gastrulation* (Genes Encode Homologous Proteins Functioning in Dorsal-Ventral Axis Formation" Cell 80(1):19-20.
Gelbart, Science, vol. 282, Oct. 23, 1998.
Hoshi, K. et al., Fibroblasts of Spinal Ligaments Pathologically Differential into Chondrocytes Induced by Recombinant Human Bone Morphogetic Protein-2: Morphological Examinations for Ossification and Spinal Ligaments. Bone vol. 21, No. 2 (Aug. 1997): 155-162.
Kim et al. (1999) "NELL-1 Enhances Mineralization in Fetal Calvarial Osteoblastic Cells." *Surgical Forum* L: 599-601.
Kuroda and Tanizawa (1999) "Involvement of Epidermal Growth Factor-like Domain of NELL Proteins in the Novel Protein—Protein Interaction with Protein Kinase C$^1$"*Biochem Biophys Res. Commun.* 265(3):752-757.
Kuroda et al. (1999) "Biochemical Characterization and Expression Analysis of Neural Thrombospondin-1-like Protein NELL1 and NELL2" *Biochem Biophys Res Common* 265(1):79-86.
Liu et al., Development Biology, vol. 166, 1994, p. 220-234.
Luce and Burrows (1999) "The neuronal EGF-related genes NELL1 and NELL2 are expressed in hemopoietic cells and developmentally regulated in the B lineage" *Gene* 231:121-126.
Opperman, L.A. et al., TGF-$\beta$1, TGF-$\beta$2, and TGF-$\beta$3 Exhbit Distinct Patterns of Expression During Cranial Suture Formation and Obliteration in Vivo and in Vitro. Journal of Bone and Mineral Research, vol. 12, No. 3 (1997): 301-310.

(Continued)

*Primary Examiner*—Vanessa L. Ford
(74) *Attorney, Agent, or Firm*—Squire Sanders & Dempsey, L.L.P.

(57) ABSTRACT

This invention pertains to the discovery that the human NELL-1 gene induces or upregulates bone mineralization. The NELL-1 gene or gene product thus provides a convenient target for screening for modulators of bone mineralization. In addition, NELL-1 can be used to facilitate repair of bone fractures and/or to generally increase bone density.

10 Claims, 2 Drawing Sheets

OTHER PUBLICATIONS

Piccolo et al. (1996) "Dorsoventral Patterning in Xenopus: Inhibition of Ventral Signals by Direct Binding of Chordin to BMP-4" *Cell* 86(4):589-498.

Siris et al., Osteoporos Int. 1998.

Takagi, K. et al. The reaction of the dura to bone morphogenetic protein (BMP) in repair of skull defects. Ann Surg. vol. 196, No. 1 (Jul. 1982): 100-109. Abstract only.

Takami, M. et al. $Ca^{2+}$-ATPase Inhibitors and $Ca^{2+}$-Ionophore Induce Osteoclast-like Cell Formation in the Cocultures of Mouse Bone Marrow Cells and Calvarial Cells. Biochemical and Biophysical Research Communications, vol. 237, 1997: 111-115. (Article No. RC977090).

Tieu A. et al. "Identification of Human NEL-2 Associated with Premature Suture Fusion." J Dent Res. 77(A):635, 1998 (Presented Mar. 4-7, 1998, Minneapolis, MN). Abstract only.

Ting et al. (1999) "Human NELL1 Expressed in Unilaterial Coronal Synostosis" *J. Bone Mineral Res.* 14(1):80-89.

Ting et al. (2000) "NELL-1 Enhances Mineralization in Fetal Calvarial Osteoblastic Cells." *J. Dent. Res.* 79:625.

Ting et al., Journal of bone and Mineral Research, vol. 14, No. 1, 1999.

Ting, K. et al. "NEL-2 Expressed in Unilateral Prematurely Fusing and Fused Coronal Sutures." J Dent Res. 77(B):2224, 1998, Abstract only.

Toriumi et al. (1991) "Manibular Reconstruction With a Recombinant Bone-Inducing Factor." *Arch. Otolaryngol. Head Neck Surg.* 117:1101-1112.

Watanabe, T.K. et al. "Cloning and Characterization of Two Novel Human cDNAs (NELL1 and NELL2) Encoding Proteins with Six EGF-like Repeats." Genomics, vol. 38, 273-276 (1996).

Wobus (Molecular Aspects of Medicine (2001), 22/3 (149-164) (Abstract only).

Yasko et al. (1992) "The Healing of Segmental Bone Defects, Induced by Recombinant Human Bone Morphogenetic Protein (rhBMP-2)." 5:659-670.

Zhang et al., (The Journal of Clinical Investigation, Sep. 2002, vol. 110, No. 6).

Liu et al., "Simultaneous Detection of Multiple Bone-Related mRNAs and Protein Expression during Osteoblast Differentiation: Polymerase Chain Reaction and Immunocytochemical Studies at the Single Cell Level", Developmental Biology, vol. 166, pp. 220-234 (1994).

Zhang et al., "NELL-1 Overexpression Transgenic Mice Simulate Human Craniosynostosis", Surgical Forum, vol. 52, pp. 576-578 (2001).

International Search Report for PCT/US2008/054779, mailed Aug. 1, 2008, 11 pgs.

Aghaloo et al., "Nell-1-induced bone regeneration in calvarial defects", Am. J. Pathol., vol. 169, pp. 903-915 (2006).

Cowan et al., "Nell-1 induced bone formation within the distracted intermaxillary suture", Bone, vol. 38, pp. 48-58 (2006).

Lu et al., "The osteoinductive properties of Nell-1 in a rat spinal fusion model", The Spine J. vol. 7, No. 1, pp. 50-60 (2007).

International Search Report for PCT/US07/83655, mailed Sep. 24, 2008, 11 pgs.

Notification of Refusal issued by JPO on Oct. 21, 2009, in connection with Appl. No. 2004-536597, 4 pgs.

Translation of a Notification of Refusal issued by JPO on Oct. 21, 2009, in connection with Appl. No. 2004-536597, 7 pgs.

Bokui Nobuyuki et al., "A biochemical analysis of new bone morphogenetic factor NELL1 which express in large amounts by serum free culture", The $75^{th}$ Ann. Meet. Of JP Biochemical Soc. 74(8) 804 (2P-595) (2002) (No translation available).

Sudou Hiroko et al., Study of Differentiation of MC3T3-E1 Osteogenetic Cells in Collagen Gel and Tissue Culture, vol. 4, No. 2, pp. 166-170 (1985) (No translation available).

\* cited by examiner

β-gal

Nell-1

Day 14 Post-Infection

Day 17 Post-Infection

Day 21 Post-Infection

NELL-1 ENHANCED BONE MINERALIZATION

CROSS-REFERENCE TO RELATED APPLICATION

This application is a continuation of U.S. application Ser. No. 09/412,297 filed on Oct. 5, 1999 now U.S. Pat. No. 7,052,856.

STATEMENT AS TO RIGHTS TO INVENTIONS MADE UNDER FEDERALLY SPONSORED RESEARCH AND DEVELOPMENT

This invention was made with Government support under Grant No. DE000422, DE094001, and RR000865 awarded by the National Institutes of Health. The Government has certain rights in this invention.

FIELD OF THE INVENTION

This invention relates to the discovery that upregulation of NELL-1 enhances bone calcification. NELL-1 thus provides a good target to screen for modulators of bone calcification. In addition, NELL-1 proteins can be used in a manner analogous to bone morphogenic proteins to facilitate bone repair.

BACKGROUND OF THE INVENTION

Defects in the process of bone repair and regeneration are linked to the development of several human diseases and disorders, e.g., osteoporosis and osteogenesis imperfecta. Failure of the bone repair mechanism is also associated with significant complications in clinical orthopedic practice, for example, fibrous non-union following bone fracture, implant interface failures and large allograft failures. The lives of many individuals would be improved by the development of new therapies designed to stimulate and strengthen the fracture repair process.

Any new technique to stimulate bone repair would be a valuable tool in treating bone fractures. A significant portion of fractured bones are still treated by casting, allowing natural mechanisms to effect wound repair. Although there have been advances in fracture treatment in recent years, including improved devices, the development of new processes to stimulate, or complement, the wound repair mechanisms would represent significant progress in this area.

A very significant patient population that would benefit from new therapies designed to promote fracture repair, or even prevent or lessen fractures, are those patients suffering from osteoporosis.

The major focus of current therapies for osteoporosis is fracture prevention, not fracture repair. This is an important consideration, as it is known that significant morbidity and mortality are associated with prolonged bed rest in the elderly, especially those who have suffered hip fracture. New methods are clearly needed for stimulating fracture repair, thus restoring mobility in these patients before the complications arise.

The techniques of bone reconstruction, such as is used to reconstruct defects occurring as a result of trauma, cancer surgery or errors in development, would also be improved by new methods to promote bone repair. Reconstructive methods currently employed, such as using autologous bone grafts, or bone grafts with attached soft tissue and blood vessels, are associated with significant drawbacks of both cost and difficulty. For example, harvesting a useful amount of autologous bone is not easily achieved, and even autologous grafts often become infected or suffer from resorption.

Several groups have investigated the possibility of using bone stimulating proteins and polypeptides, particularly recombinant bone morphogenic proteins (BMPs), to influence bone repair in vivo. For example, recombinant BMP-2 has been employed to repair surgically created defects in the mandible of adult dogs (Toriumi et al. (1991) *Arch. Otolaryngol. Head Neck Surg.* 117: 1101-1112), and high doses of this molecule have been shown to functionally repair segmental defects in rat femurs (Yasko et al. (1992) *J. Bone Joint Surg.* 5: 659-670). Chen and colleagues showed that a single application of 25-100 mg of recombinant TGF-β adjacent to cartilage induced endochondral bone formation in the rabbit ear full thickness skin wounds (Chen et al. (1991) *Biol. Chem.* 268: 27381-27389). It has also been reported that an application of TGF-.beta.1 in a 3% methylcellulose gel was able to repair surgically induced large skull defects that otherwise heal by fibrous connective tissue and never form bone (Beck et al. (1991) *Bone Miner. Res.* 11:1257-1265).

Inspired by these early successes alternative therapies using osteogenic compositions are desired.

SUMMARY OF THE INVENTION

This invention pertains to the discovery that the polypeptide encoded by the human NELL-1 gene induces bone mineralization and is therefore osteogenic. The NELL-1 gene and gene product(s) (e.g. mRNA cDNA, protein, etc.) provide good targets for screening for modulators of NELL-1 expression and/or activity and therefore for modulators of bone mineralization. In addition, NELL-1 can be used in a manner analogous to the use of bone morphogenic proteins (BMPs) to speed fracture repair and as a component of bone graft materials.

As indicated, in one preferred embodiment, this invention provides methods of screening for an agent that alters bone mineralization. The methods involve contacting a cell containing a NELL-1 gene with a test agent; and detecting a change in the expression level of the NELL-1 gene as compared to the expression of the NELL-1 gene in a cell that is not contacted with the test agent where a difference in the expression level (e.g. as represented by genomic DNA copy number, mRNA level, protein level, protein activity, etc.), of NELL-1 in the contacted cell and the cell that is not contacted indicates that said agent modulates bone mineralization. The methods may further involve test agents that alter expression of the NELL-1 nucleic acid or the NELL-1 protein in a database of modulators of NELL-1 activity or in a database of modulators of bone mineralization. In certain embodiments, the expression level of NELL-1 is detected by measuring the level of NELL-1 mRNA in the cell (e.g. by hybridizing said mRNA to a probe that specifically hybridizes to a NELL-1 nucleic acid). Preferred hybridization methods include, but are not limited to a Northern blot, a Southern blot using DNA derived from the NELL-1 RNA, an array hybridization, an affinity chromatography, and an in situ hybridization. The methods of this invention are amenable to array-based approaches. Thus, in some embodiments, the probe is a member of a plurality of probes that forms an array of probes. The level of NELL-1 expression can also be determined using a nucleic acid amplification reaction (e.g. PCR).

In other embodiments of the screening systems of this invention, NELL-1 expression is detected by determining the expression level of a NELL-1 protein (e.g. via of capillary electrophoresis, a Western blot, mass spectroscopy, ELISA, immunochromatography, immunohistochemistry, etc.) in the biological sample. The cell can be cultured ex vivo or can be in vivo and/or in situ. In certain embodiments, the test agent is not an antibody and/or not a protein and/or not a nucleic acid. Preferred test agents are small organic molecules.

This invention also provides methods of prescreening for a potential modulator of NELL-1 expression and/or activity. The methods involve contacting a NELL-1 nucleic acid or a NELL-1 protein with a test agent; and detecting specific binding of said test agent to the NELL-1 protein or nucleic acid. The method can further involve recording test agents that specifically bind to the NELL-1 nucleic acid or to said NELL-1 protein in a database of candidate modulators of NELL-1 activity and/or in a database of candidate modulators of bone mineralization. The test agent can be contacted directly to the NELL-1 nucleic acid and/or protein, or to a cell and/or tissue and/or organism (e.g., mammal) containing the nucleic acid and/or protein. Where a cell is contacted, the cell can be in a primary or passaged culture. In certain embodiments, the test agent is not an antibody and/or not a protein and/or not a nucleic acid. Preferred test agents are small organic molecules. Where the assay measures the ability of the test agent to bind to a nucleic acid, preferred assays utilize a Northern blot, a Southern blot using DNA, an array hybridization, an affinity chromatography, or an in situ hybridization. Where the assay measures the ability of the test agent to bind to a NELL-1 protein, preferred assays utilize capillary electrophoresis, a Western blot, mass spectroscopy, ELISA, immunochromatography, or immunohistochemistry).

In another embodiment, this invention provides methods of increasing bone mineralization. Preferred methods involve increasing the concentration of a NELL-1 gene product in an osteogenic cell (e.g. an osteoblast, a mesenchymal cell, a fibroblast cell, a fetal embryonic cell, a stem cell, a bone marrow cell, a dura cell, a chrondrocyte, a chondroblast, etc.) or in the milieu within which the cell is found. In one preferred embodiment, the concentration of NELL-1 gene product is increased by upregulating expression of a NELL-1 gene. This can be accomplished by any of a wide variety of methods including, but not limited to upregulating expression of an endogenous NELL-1 gene (e.g. by modifying the endogenous regulatory region e.g. the promoter), or transfecting the cell with a vector that expresses a NELL-1 protein. Certain preferred vectors constitutively expresses a NELL-1 protein, while other preferred vectors are inducible. In still another embodiment, the NELL-1 gene product concentration is increased by the bone with a NELL-1 polypeptide.

This invention also provides methods of facilitating the repair of bone fractures. These methods involve increasing concentration of a NELL-1 gene product at or near the fracture site. In preferred embodiments, the NELL-1 gene product is increased in an osteogenic or bone precursor cell present at or near the fracture site. The methods can involve introducing an osteogenic cell or bone precursor cell that overexpresses NELL-1 into the fracture site. In another embodiment, this invention can involve increasing the concentration of a NELL-1 gene product in the osteogenic cell or said bone precursor cell in situ. The NELL-1 gene product up-regulation can be achieved as described herein. In another embodiment, the cell and/or bone fracture site is contacted with a NELL-1 polypeptide.

In another approach to fracture repair, the fracture site is contacted with a NELL-1 protein. The protein can be produced by a cell (e.g. introduced by introduction of a cell overexpressing NELL-1 protein) and/or by administration of the protein alone or in combination with a pharmacological excipient, and/or by administration of a "naked DNA" vector capable of expressing NELL-1. The NELL-1 protein can be a component of a bone repair/bone graft material and/or part of a prosthetic device. One preferred graft material includes collagen and/or bone fragments in addition to the NELL-1 protein and/or cells expressing a NELL-1 protein.

In still yet another embodiment this invention provides a bone graft material capable of enhancing the formation of osseous tissue in the animal in which it is implanted. Preferred bone graft materials consist essentially of a biocompatible matrix and a NELL-1 protein. A preferred graft material is resorbable/biodegradable. Again, the matrix can be impregnated with a NELL-1 protein and/or a cell expressing a NELL-1 protein. A preferred bone graft material comprises a collagen conjugate containing: (e.g., about 65 to about 95 weight percent) reconstituted collagen having dispersed substantially uniformly therein; and (e.g., about 35 to about 5 weight percent) a NELL-1 protein and/or a cell expressing a NELL-1 protein.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "NELL-1 cDNA" and "NELL-1 " genomic DNA refer to the cDNA and genomic DNA as disclosed by Watanabe et al. (1996) *Genomics* 38 (3): 273-276; Ting et al. (1999) *J Bone Mineral Res,* 14: 80-89; and GenBank Accession Number U57523).

A NELL-1 protein is a protein expressed by the NELL-1 gene or cDNA. The NELL-1 protein can include NELL-1 protein fragments that retain the ability to induce bone mineralization.

The term "antibody", as used herein, includes various forms of modified or altered antibodies, such as an intact immunoglobulin, an Fv fragment containing only the light and heavy chain variable regions, an Fv fragment linked by a disulfide bond (Brinkmann et al. (1993) *Proc. Natl. Acad. Sci. USA,* 90: 547-551), an Fab or (Fab)'2 fragment containing the variable regions and parts of the constant regions, a single-chain antibody and the like (Bird et al. (1988) *Science* 242: 424-426; Huston et al. (1988) *Proc. Nat. Acad. Sci. USA* 85: 5879-5883). The antibody may be of animal (especially mouse or rat) or human origin or may be chimeric (Morrison et al. (1984) *Proc Nat. Acad. Sci. USA* 81: 6851-6855) or humanized (Jones et al. (1986) *Nature* 321: 522-525, and published UK patent application #8707252).

The terms "binding partner", or "capture agent", or a member of a "binding pair" refers to molecules that specifically bind other molecules to form a binding complex such as antibody-antigen, lectin-carbohydrate, nucleic acid-nucleic acid, biotin-avidin, etc.

The term "specifically binds", as used herein, when referring to a biomolecule (e.g., protein, nucleic acid, antibody, etc.), refers to a binding reaction which is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The term osteoporosis refers to a heterogeneous group of disorders characterized by decreased bone mass and fractures. Clinically, osteoporosis is segregated into type I and type II. Type I osteoporosis occurs predominantly in middle aged women and is associated with estrogen loss at the menopause, while osteoporosis type II is associated with advancing age.

Osteogenesis imperfecta (OI) refers to a group of inherited connective tissue diseases characterized by bone and soft connective tissue fragility (Byers & Steiner (1992) *Annu. Rev. Med.* 43: 269-289; Prockop (1990) *J. Biol. Chem.* 265: 15349-15352). Males and females are affected equally, and the overall incidence is currently estimated to be 1 in 5,000-14,000 live births. Hearing loss, dentinogenesis imperfecta, respiratory insufficiency, severe scoliosis and emphysema are just some of the conditions that are associated with one or more types of OI. While accurate estimates of the health care costs are not available, the morbidity and mortality associated with OI certainly result from the extreme propensity to fracture (OI types I-IV) and the deformation of abnormal bone following fracture repair (OI types II-IV).

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt 2, Overview of principles of hybridization and the strategy of nucleic acid probe assays*, Elsevier, NY (Tijssen). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1-3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

"Osteogenic cells" are cells capable of mineralizing. Osteogenic cells include osteoblasts, osteoblast like cells, mesenchymal cells, fibroblast cells, fetal embryonic cells, stem cells, bone marrow cells, dura cells, chrondrocyes, and chondroblastic cells.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intranet, data or databases stored in specialized hardware (e.g. in microchips), and the like.

DETAILED DESCRIPTION

Figure 1A:
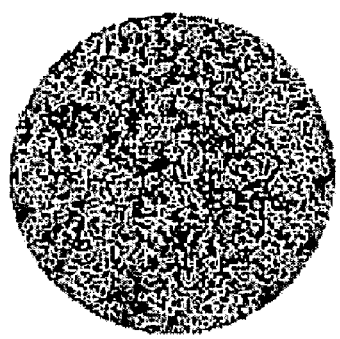
FIG. 1A illustrates over-expression of NELL-1 in E-14 rat calvarial primary cell cultures using adenoviruses with β-galactosidase as control.
Figure 1A:
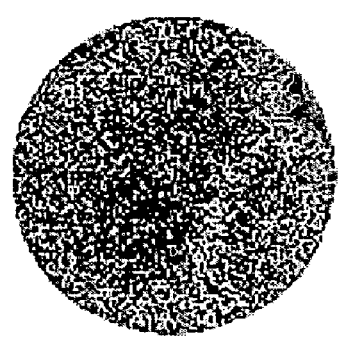
Figure 1A:
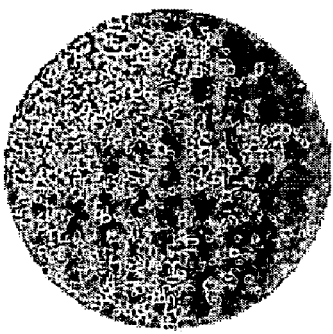
Figure 1A:
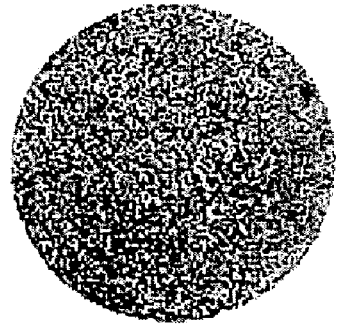
Figure 1A:
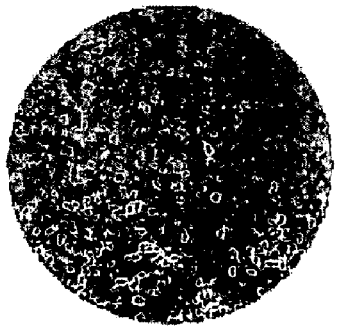
Figure 1A:
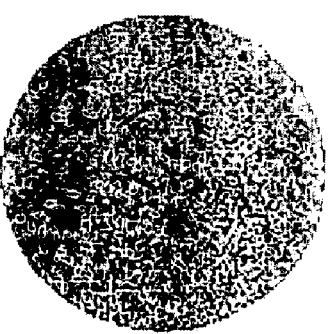
Figure 1B:
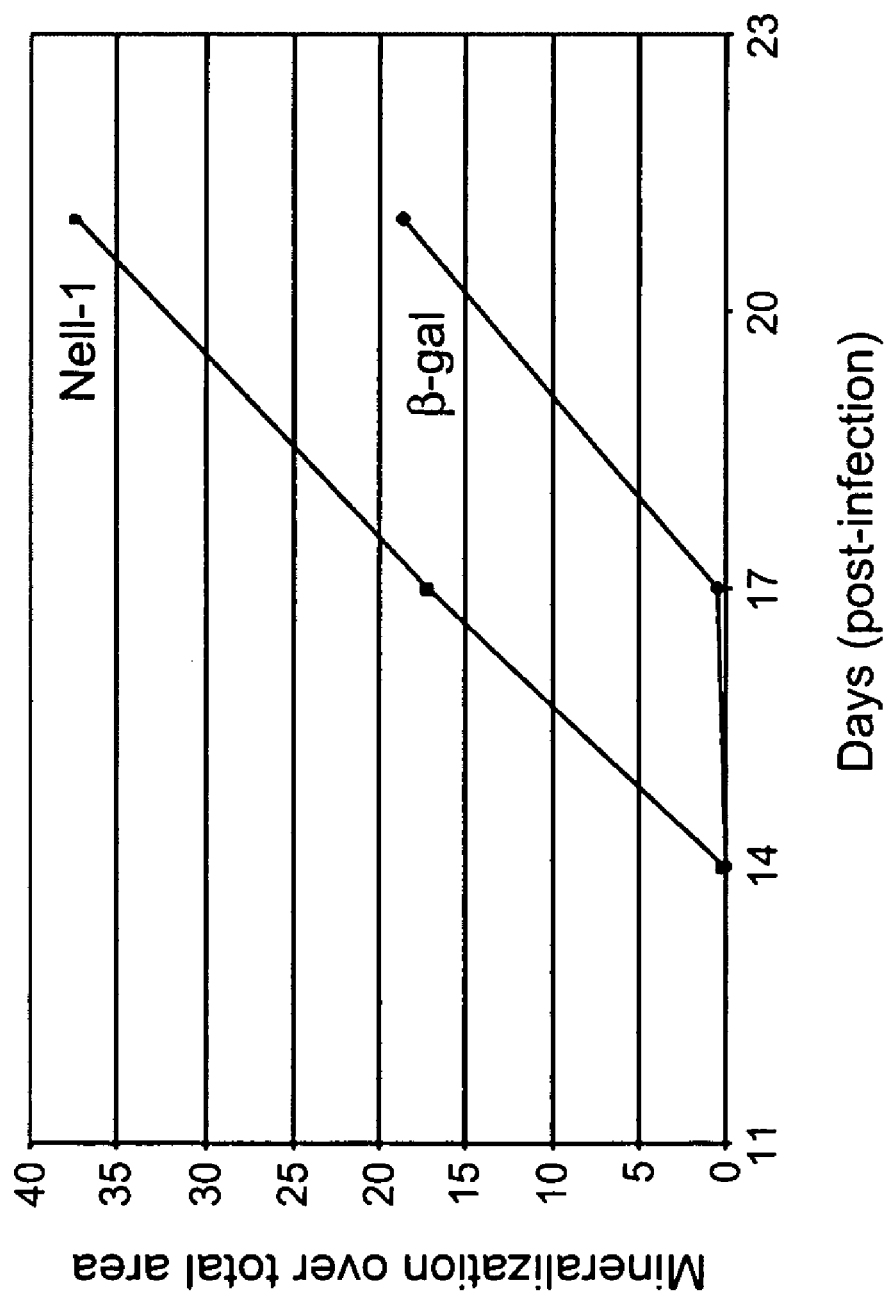
FIG. 1B shows a plot of mineralization as a function of time post treatment with NELL-1 and β-galactosidase respectively. Experiments were performed in triplicate. Student's T test was performed. Mineralization with NELL-1 was statistically higher than mineralization with β-Galactosidase control, *P<0.001.

This invention provides pertains to the discovery that the NELL-1 gene product enhances tissue (e.g. bone) mineralization. Without being bound to a particular theory, it is believed that the NELL-1 protein may execute its function by interacting with members of the TGFβ superfamily.

Having recognized that NELL-1 mediates tissue mineralization as described herein, NELL-1 nucleic acids and/or NELL-1 proteins provide convenient targets for screening for modulators of bone mineralization. Thus agents that inhibit NELL-1 expression and/or protein activity and/or protein-protein interactions will decrease bone mineralization. Conversely agents that upregulate NELL-1 expression and/or protein activity and/or protein-protein interactions are expected to increase bone mineralization. Such NELL-1 "agonists" are expected to be useful in a wide variety of contexts including, but not limited treatment of osteoporosis, bone fracture healing, treatment of osteogenesis imperfecta, bone reconstruction, and the like.

Thus, in one embodiment, this invention provides methods of identifying agents that modulate (e.g. up-regulate or down-regulate) NELL-1 expression. Such methods involve contacting a NELL-1 nucleic acid, and/or a cell containing a NELL-1 nucleic acid, and/or a tissue or organism comprising cells containing a NELL-1 nucleic acid and detecting changes in the level of NELL-1 transcript (e.g. mRNA) and/or NELL-1 protein. In one embodiment, candidate test agents for such an assay are identified in a binding assay "pre-screen". Such a binding assay involves pre-screening test agent(s) for the ability to specifically bind to a NELL-1 nucleic acid and/or a NELL-1 protein. Agents identified by theses assays that upregulate NELL-1 expression are expected to be useful in the treatment of osteoporosis and bone fractures.

In addition, in a manner analogous to the use of bone morphogenic proteins (e.g. BMP-1 through BMP-24), the NELL-1 polypeptide(s) can be used to speed repair of bone fractures or to induce bone repair or replacement under circumstances where natural healing is limited or non-existent. In generally such methods involve increasing the amount of a NELL-1 gene product at or near the fracture site in a bone. The NELL-1 gene product concentration can be increased by one or more of a number of methods. In one approach, cells at or near the bone fracture site are induced to express elevated levels of NELL-1. This is accomplished, for example, by the use of modulators of NELL-1 expression, by altering the NELL-1 promoter, or by transfecting the cell with a construct that expresses NELL-1. This can be accomplished in vivo, or, in another embodiment, such cells can be modified to over-express NELL-1 ex vivo and then introduced back into the subject organism (e.g. at or near a fracture site).

Cells expressing or overexpressing NELL-1 can be incorporated into bone graft materials and/or NELL-1 polypeptides can be incorporated into such bone graft materials. These graft materials can be used in the treatment of fractures or to facilitate the replacement/healing of prostheses or bone transplants.

I. Assays for Agents that Modulate NELL-1 Expression.

As indicated above, in one aspect, this invention is premised on the discovery that NELL-1 mediates mineralization of bone and thus provides a good target for new agents that modulate bone mineralization. Thus, in one embodiment, this invention provides methods of screening for agents that modulate NELL-1 expression and hence bone mineralization. The methods involve detecting the expression level and/or activity level of a NELL-1 gene or gene product (e.g. NELL-1 protein) in the presence of the agent(s) in question. An elevated NELL-1 expression level or activity level in the presence of the agent as compared to a negative control where the test agent is absent or at reduced concentration indicates that the agent upregulates NELL-1 activity or expression. Conversely, decreased NELL-1 expression level or activity level in the presence of the agent as compared to a negative control where the test agent is absent or at reduced concentration indicates that the agent down-regulates NELL-1 activity or expression Expression levels of a gene can be altered by changes in by changes in the transcription of the gene product (i.e. transcription of mRNA), and/or by changes in translation of the gene product (i.e. translation of the protein), and/or by post-translational modification(s) (e.g. protein folding, glycosylation, etc.). Thus preferred assays of this invention include assaying for level of transcribed mRNA (or other nucleic acids derived from the NELL-1 gene), level of translated protein, activity of translated protein, etc. Examples of such approaches are described below.

A) Nucleic-Acid Based Assays.

1) Target Molecules.

Changes in expression level can be detected by measuring changes in mRNA and/or a nucleic acid derived from the mRNA (e.g. reverse-transcribed cDNA, etc.). In order to measure the NELL-1 expression level it is desirable to provide a nucleic acid sample for such analysis. In preferred embodiments the nucleic acid is found in or derived from a biological sample. The term "biological sample", as used herein, refers to a sample obtained from an organism or from components (e.g., cells) of an organism. The sample may be of any biological tissue or fluid. Biological samples may also include organs or sections of tissues such as frozen sections taken for histological purposes.

The nucleic acid (e.g., mRNA nucleic acid derived from mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation*, Elsevier, N.Y. and Tijssen ed.

In a preferred embodiment, the "total" nucleic acid is isolated from a given sample using, for example, an acid guanidinium-phenol-chloroform extraction method and polyA+ mRNA is isolated by oligo dT column chromatography or by using (dT)n magnetic beads (see, e.g., Sambrook et al., Molecular Cloning: A Laboratory Manual (2nd ed.), Vols. 1-3, Cold Spring Harbor Laboratory, (1989), or Current Protocols in Molecular Biology, F. Ausubel et al., ed. Greene Publishing and Wiley-Interscience, New York (1987)).

Frequently, it is desirable to amplify the nucleic acid sample prior to assaying for expression level. Methods of amplifying nucleic acids are well known to those of skill in the art and include, but are not limited to polymerase chain reaction (PCR, see. e.g., Innis, et al., (1990) *PCR Protocols. A guide to Methods and Application*. Academic Press, Inc. San Diego,), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In a particularly preferred embodiment, where it is desired to quantify the transcription level (and thereby expression) of NELL-1 in a sample, the nucleic acid sample is one in which the concentration of the NELL-1 mRNA transcript(s), or the concentration of the nucleic acids derived from the NELL-1 mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, the NELL-1-containing nucleic acid sample is the total mRNA or a total cDNA isolated and/or otherwise derived from a biological sample. The nucleic acid may be isolated from the sample according to any of a number of methods well known to those of skill in the art as indicated above.

2) Hybridization-Based Assays.

Using the known sequence of NELL-1 (see, e.g., SEQ ID No: 1) detecting and/or quantifying the NELL-1 transcript(s) can be routinely accomplished using nucleic acid hybridization techniques (see, e.g., Sambrook et al. supra). For example, one method for evaluating the presence, absence, or quantity of NELL-1 reverse-transcribed cDNA involves a "Southern Blot". In a Southern Blot, the DNA (e.g., reverse-transcribed NELL-1 mRNA), typically fragmented and separated on an electrophoretic gel, is hybridized to a probe specific for NELL-1. Comparison of the intensity of the hybridization signal from the NELL-1 probe with a "control" probe (e.g. a probe for a "housekeeping gene") provides an estimate of the relative expression level of the target nucleic acid.

Alternatively, the NELL-1 mRNA can be directly quantified in a Northern blot. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target NELL-1 mRNA. Appropriate controls (e.g. probes to housekeeping genes) provide a reference for evaluating relative expression level.

An alternative means for determining the NELL-1 expression level is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In some applications it is necessary to block the hybridization capacity of repetitive sequences. Thus, in some embodiments, tRNA, human genomic DNA, or Cot-1 DNA is used to block non-specific hybridization.

3) Amplification-Based Assays.

In another embodiment, amplification-based assays can be used to measure NELL-1 expression (transcription) level. In such amplification-based assays, the target nucleic acid sequences (i.e., NELL-1) act as template(s) in amplification reaction(s) (e.g. Polymerase Chain Reaction (PCR) or reverse-transcription PCR (RT-PCR)). In a quantitative amplification, the amount of amplification product will be proportional to the amount of template (e.g., NELL-1 mRNA) in the original sample. Comparison to appropriate (e.g. healthy tissue or cells unexposed to the test agent) controls provides a measure of the NELL-1 transcript level.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). One approach, for example, involves simultaneously co-amplifying a known quantity of a control sequence using the same primers as those used to amplify the target. This provides an internal standard that may be used to calibrate the PCR reaction.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of labeled nucleic acid (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al. (1990) Academic Press, Inc. N.Y. The known nucleic acid sequence(s) for NELL-1 are sufficient to enable one of skill to routinely select primers to amplify any portion of the gene.

4) Hybridization Formats and Optimization of Hybridization Conditions.

a) Array-Based Hybridization Formats.

In one embodiment, the methods of this invention can be utilized in array-based hybridization formats. Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958, Pinkel et al. (1998) *Nature Genetics* 20: 207-211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays. Synthesis of high density arrays is also described in U.S. Pat. Nos. 5,744, 305, 5,800,992 and 5,445,934.

b) Other Hybridization Formats.

As indicated above a variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach*, IRL Press; Gall and Pardue (1969) *Proc. Natl. Acad. Sci. USA* 63: 378-383; and John et al. (1969) *Nature* 223: 582-587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3H$, $^{125}I$, $^{35}S$, $^{14}C$, or $^{32}P$-labelled probes or the like. Other labels include ligands that bind to labeled antibodies, fluorophores, chemi-luminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

c) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce nonspecific binding. The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105-114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

d) Labeling and Detection of Nucleic Acids.

The probes used herein for detection of NELL-1 expression levels can be full length or less than the full length of the NELL-1 mRNA. Shorter probes are empirically tested for specificity. Preferred probes are sufficiently long so as to specifically hybridize with the NELL-1 target nucleic acid(s) under stringent conditions. The preferred size range is from about 20 bases to the length of the NELL-1 mRNA, more preferably from about 30 bases to the length of the NELL-1 mRNA, and most preferably from about 40 bases to the length of the NELL-1 mRNA.

The probes are typically labeled, with a detectable label. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish sites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescent labels should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science,* 281: 2013-2016). Similarly, highly fluorescent quantum dots (zinc sulfide-capped cadmium selenide) have been covalently coupled to biomolecules for use in ultrasensitive biological detection (Warren and Nie (1998) *Science,* 281: 2016-2018).

B) Polypeptide-Based Assays.

1) Assay Formats.

In addition to, or in alternative to, the detection of NELL-1 nucleic acid expression level(s), alterations in expression of NELL-1 can be detected and/or quantified by detecting and/or quantifying the amount and/or activity of translated NELL-1 polypeptide.

2) Detection of Expressed Protein

The polypeptide(s) encoded by the NELL-1 can be detected and quantified by any of a number of methods well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one preferred embodiment, the NELL-1 polypeptide(s) are detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purification,* Springer-Verlag, N.Y.; Deutscher, (1990) *Methods in Enzymology Vol.* 182*: Guide to Protein Purification,* Academic Press, Inc., N.Y.).

In another preferred embodiment, Western blot (immunoblot) analysis is used to detect and quantify the presence of polypeptide(s) of this invention in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target polypeptide(s) and may be directly labeled or alternatively may be subsequently detected using labeled antibodies (e.g., labeled sheep anti-mouse antibodies) that specifically bind to the a domain of the antibody.

In preferred embodiments, the NELL-1 polypeptide(s) are detected using an immunoassay. As used herein, an immunoassay is an assay that utilizes an antibody to specifically bind to the analyte (e.g., the target polypeptide(s)). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376,110; 4,517,288; and 4,837,168) are well suited to detection or quantification of the polypeptide(s) identified herein. For a review of the general immunoassays, see also Asai (1993) *Methods in Cell Biology Volume* 37*: Antibodies in Cell Biology,* Academic Press, Inc. New York; Stites & Terr (1991) *Basic and Clinical Immunology* 7*th Edition.*

Immunological binding assays (or immunoassays) typically utilize a "capture agent" to specifically bind to and often immobilize the analyte (NELL-1 polypeptide). In preferred embodiments, the capture agent is an antibody.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401-1406, and Akerstrom (1985) *J. Immunol.,* 135: 2589-2542).

Preferred immunoassays for detecting the target polypeptide(s) are either competitive or noncompetitive. Noncompetitive immunoassays are assays in which the amount of captured analyte is directly measured. In one preferred "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (NELL-1 polypeptide) present in the sample is measured indirectly by measuring the amount of an added (exogenous) analyte displaced (or competed away) from a capture agent (antibody) by the analyte present in the sample. In one competitive assay, a known amount of, in this case, labeled polypeptide is added to the sample and the sample is then contacted with a capture agent. The amount of labeled polypeptide bound to the antibody is inversely proportional to the concentration of target polypeptide present in the sample.

In one particularly preferred embodiment, the antibody is immobilized on a solid substrate. The amount of target polypeptide bound to the antibody may be determined either by measuring the amount of target polypeptide present in an polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies that bind NELL-1 polypeptide(s), either alone or in combination. In the case where the antibody that binds NELL-1 polypeptide is not labeled, a different detectable marker, for example, an enzyme-labeled antibody capable of binding to the monoclonal antibody which binds the NELL-1 polypeptide, may be employed. Any of the known modifications of EIA, for example, enzyme-linked immunoabsorbent assay (ELISA), may also be employed. As indicated above, also contemplated by the present invention are immunoblotting immunoassay techniques such as western blotting employing an enzymatic detection system.

The immunoassay methods of the present invention may also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection systems, and the like.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. In certain embodiments, the amount of antibody that binds NELL-polypeptides is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents may also be included.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein, are commercially available or can be produced as described below.

3) Antibodies to NELL-1 Polypeptides.

Either polyclonal or monoclonal antibodies may be used in the immunoassays of the invention described herein. Polyclonal antibodies are preferably raised by multiple injections (e.g. subcutaneous or intramuscular injections) of substantially pure polypeptides or antigenic polypeptides into a suitable non-human mammal. The antigenicity of the target peptides can be determined by conventional techniques to determine the magnitude of the antibody response of an animal that has been immunized with the peptide. Generally, the peptides that are used to raise antibodies for use in the methods of this invention should generally be those which induce production of high titers of antibody with relatively high affinity for target polypeptides encoded by NELL-1.

If desired, the immunizing peptide may be coupled to a carrier protein by conjugation using techniques that are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit).

The antibodies are then obtained from blood samples taken from the mammal. The techniques used to develop polyclonal antibodies are known in the art (see, e.g., *Methods of Enzymology*, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies see, for example, Coligan, et al. (1991) Unit 9, *Current Protocols in Immunology*, Wiley Interscience).

Preferably, however, the antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and $F(ab')^{2'}$, and/or single-chain antibodies (e.g. scFv) which are capable of binding an epitopic determinant. Also, in this context, the term "mab's of the invention" refers to monoclonal antibodies with specificity for a polypeptide encoded by a NELL-1 polypeptide.

The general method used for production of hybridomas secreting mAbs is well known (Kohler and Milstein (1975) *Nature*, 256:495). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines. Confirmation of specificity among mAb's can be accomplished using relatively routine screening techniques (such as the enzyme-linked immunosorbent assay, or "ELISA") to determine the elementary reaction pattern of the mAb of interest.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) *Nature*, 348: 552-554; Hoogenboom et al. (1991) *Nucleic Acids Res.* 19: 41334137).

Since the antibody fragments on the surface of the phage are functional, phage bearing antigen binding antibody fragments can be separated from non-binding phage by antigen affinity chromatography (McCafferty et al. (1990) *Nature*, 348: 552-554). Depending on the affinity of the antibody fragment, enrichment factors of 20 fold-1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature*, 348: 552-554). Thus even when enrichments are low (Marks et al. (1991) *J. Mol. Biol.* 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol.* 222: 581-597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol.* 222: 581-597; Marks et al. (1993). *Bio/Technology.* 10: 779-783; Griffiths et al. (1993) *EMBO J.* 12: 725-734; Clackson et al. (1991) *Nature.* 352: 624-628). Antibodies have been produced against self proteins, including human thyroglobulin, immunoglobulin, tumor necrosis factor and CEA (Griffiths et al. (1993) *EMBO J.* 12: 725-734). It is also possible to isolate antibodies against cell surface antigens by selecting directly on intact cells. The antibody fragments are highly specific for the antigen used for selection and have affinities in the 1 µM to 100 nM range (Marks et al. (1991) *J. Mol. Biol.* 222: 581-597; Griffiths et al. (1993) *EMBO J.* 12: 725-734). Larger phage antibody libraries result in the isolation of more antibodies of higher binding affinity to a greater proportion of antigens.

It will also be recognized that antibodies can be prepared by any of a number of commercial services (e.g., Berkeley antibody laboratories, Bethyl Laboratories, Anawa, Eurogenetec, etc.).

C) Assay Optimization.

The assays of this invention have immediate utility in screening for agents that modulate the NELL-1 expression of a cell, tissue or organism. The assays of this invention can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred PCR conditions), hybridization conditions that maximize signal to noise, protocols that improve throughput, etc. In addition, assay formats can be selected and/or optimized according to the availability of equipment and/or reagents. Thus, for example, where commercial antibodies or ELISA kits are available it may be desired to assay protein concentration. Conversely, where it is desired to screen for modulators that alter transcription the NELL-1 gene, nucleic acid based assays are preferred.

Routine selection and optimization of assay formats is well known to those of ordinary skill in the art.

II. Pre-Screening for Agents that Bind NELL-1

In certain embodiments it is desired to pre-screen test agents for the ability to interact with (e.g. specifically bind to) a NELL-1 nucleic acid or polypeptide. Specifically binding test agents are more likely to interact with and thereby modulate NELL-1 expression and/or activity. Thus, in some preferred embodiments, the test agent(s) are pre-screened for binding to NELL-1 nucleic acids or to NELL-1 proteins before performing the more complex assays described above.

In one embodiment, such pre-screening is accomplished with simple binding assays. Means of assaying for specific binding or the binding affinity of a particular ligand for a nucleic acid or for a protein are well known to those of skill in the art. In preferred binding assays, the NELL-1 protein or nucleic acid is immobilized and exposed to a test agent (which can be labeled), or alternatively, the test agent(s) are immobilized and exposed to an NELL-1 protein or to a NELL-1 nucleic acid (which can be labeled). The immobilized moiety is then washed to remove any unbound material and the bound test agent or bound NELL-1 nucleic acid or protein is detected (e.g. by detection of a label attached to the bound molecule). The amount of immobilized label is proportional to the degree of binding between the NELL-1 protein or nucleic acid and the test agent.

III. Agents for Screening.

While, in one embodiment, the assays described above provided methods of detecting the presence or absence, or quantifying expression of NELL-1, it will be appreciated that the same assays can be used to screen for agents that modulate the expression of and/or the activity of an MT-SP1 serine protease. To screen for potential modulators, the assays described above are performed in the presence of one or more test agents or are performed using biological samples from cells and/or tissues and/or organs and/or organisms exposed to one or more test agents. The MT-SP1 activity and/or expression level is determined and, in a preferred embodiment, compared to the activity level(s) observed in "control" assays (e.g., the same assays lacking the test agent). A difference between the MT-SP1 expression and/or activity in the "test" assay as compared to the control assay indicates that the test agent is a "modulator" of SP1 expression and/or activity.

In a preferred embodiment, the assays of this invention level are deemed to show a positive result, e.g. elevated expression and/or MT-SP1 activity, genes, when the measured protein or nucleic acid level or protein activity is greater than the level measured or known for a control sample (e.g. either a level known or measured for a normal healthy cell, tissue or organism mammal of the same species not exposed to the or putative modulator (test agent), or a "baseline/reference" level determined at a different tissue and/or a different time for the same individual). In a particularly preferred embodiment, the assay is deemed to show a positive result when the difference between sample and "control" is statistically significant (e.g. at the 85% or greater, preferably at the 90% or greater, more preferably at the 95% or greater and most preferably at the 98% or greater confidence level).

IV. High Throughput Screening.

The assays of this invention are also amenable to "high-throughput" modalities. Conventionally, new chemical entities with useful properties (e.g., modulation of NELL-1 expression or activity) are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of compounds (candidate compounds) potentially having the desired activity. Such "combinatorial chemical libraries"

are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A) Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) Int. J. Pept. Prot. Res., 37: 487-493, Houghton et al. (1991) Nature, 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) Proc. Nat. Acad. Sci. USA 90: 6909-6913), vinylogous polypeptides (Hagihara et al. (1992) J. Amer. Chem. Soc. 114: 6568), nonpeptidal peptidomimetics with a Beta-D-Glucose scaffolding (Hirschmann et al., (1992) J. Amer. Chem. Soc. 114: 9217-9218), analogous organic syntheses of small compound libraries (Chen et al. (1994) J. Amer. Chem. Soc. 116: 2661), oligocarbamates (Cho, et al., (1993) Science 261:1303), and/or peptidyl phosphonates (Campbell et al., (1994) J. Org. Chem. 59: 658). See, generally, Gordon et al., (1994) J. Med. Chem. 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) Nature Biotechnology, 14(3): 309-314), and PCT/US96/10287), carbohydrate libraries (see, e.g., Liang et al. (1996) Science, 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

B) High Throughput Assays of Chemical Libraries.

Any of the assays for that modulate expression of NELL-1 or that alter the binding specificity and/or activity of NELL-1 polypeptides are amenable to high throughput screening. As described above, having determined that NELL-1 expression is associated with bone mineralization, likely modulators either inhibit or increase bone mineralization. Preferred assays thus detect inhibition of transcription (i.e., inhibition of mRNA production) by the test compound(s), inhibition of protein expression by the test compound(s), or binding to the gene (e.g., gDNA, or cDNA) or gene product (e.g., mRNA or expressed protein) by the test compound(s). Alternatively, the assay can detect inhibition of the characteristic activity of the NELL-1 polypeptide.

High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

V. Increasing Bone Mineralization Using NELL-1 Nucleic Acids and/or Polypeptides.

In still another embodiment, this invention provides methods and compositions to enhance bone growth. This is useful in a variety of contexts including, but not limited to, bone reconstruction, such as is used to reconstruct defects occurring as a result of trauma, cancer surgery or errors in development. the treatment of osteogenesis imperfecta, the treatment of osteoporosis, and the healing of major or minor bone fractures.

The methods generally involve increasing NELL-1 protein concentration at or near a bone or at or in a bone progenitor cell and/or contacting a cell (e.g. a bone progenitor cell) with a NELL-1 polypeptide or with a vector encoding a NELL-1 polypeptide. This can be accomplished by transforming a bone precursor cell so that it expresses elevated levels of endogenous NELL-1 or so that it expresses NELL-1 from an exogenous transfected NELL-1 nucleic acid, or by contacting the bone, bone fracture site, bone precursor cells with NELL-1 protein(s) or local or systemic administration of a NELL-1 protein.

As used herein, the term "bone progenitor cells" refers to any or all of those cells that have the capacity to ultimately form, or contribute to the formation of, new bone tissue. This includes various cells in different stages of differentiation, such as, for example, stem cells, macrophages, fibroblasts, vascular cells, osteoblasts, chondroblasts, osteoclasts, and the like. Bone progenitor cells also include cells that have been isolated and manipulated in vitro, e.g., subjected to stimulation with agents such as cytokines or growth factors or even genetically engineered cells. The particular type or types of bone progenitor cells that are stimulated using the methods and compositions of the invention are not important, so long as the cells are stimulated in such a way that they are activated and, in the context of in vivo embodiments, ultimately give rise to new bone tissue.

The term "bone progenitor cell" is also used to particularly refer to those cells that are located within, are in contact with, or migrate towards (i.e., "home to"), bone progenitor tissue and which cells directly or indirectly stimulate the formation of mature bone. As such, the progenitor cells may be cells that ultimately differentiate into mature bone cells themselves, i.e., cells that "directly" form new bone tissue. Cells that, upon stimulation, attract further progenitor cells or promote nearby cells to differentiate into bone-forming cells (e.g., into osteoblasts, osteocytes and/or osteoclasts) are also considered to be progenitor cells in the context of this disclosure—as their stimulation "indirectly" leads to bone repair or regeneration. Cells affecting bone formation indirectly may do so by the elaboration of various growth factors or cytokines, or by their physical interaction with other cell types. The direct or indirect mechanisms by which progenitor cells stimulate bone repair is not necessary a consideration in practicing this invention. Bone progenitor cells and bone progenitor tissues may be cells and tissues that, in their natural environment, arrive at an area of active bone growth, repair or regeneration. In terms of bone progenitor cells, these may also be cells that are attracted or recruited to such an area. These may be cells that are present within an artificially-created osteotomy site in an animal model. Bone progenitor cells may also be isolated from animal or human tissues and maintained in an in vitro environment. Suitable areas of the body from which to obtain bone progenitor cells are areas such as the bone tissue and fluid surrounding a fracture or other skeletal defect (whether or not this is an artificially created site), or indeed, from the bone marrow. Isolated cells may be stimulated using the methods and compositions disclosed herein and, if desired, be returned to an appropriate site in an animal where bone repair is to be stimulated. In such cases, the nucleic-acid containing cells would themselves be a form of therapeutic agent. Such ex vivo protocols are well known to those of skill in the art. In preferred embodiments of the invention, the bone progenitor cells and tissues will be those cells and tissues that arrive at the area of bone fracture or damage that one desires to treat. Accordingly, in treatment embodiments, there is no difficulty associated with the identification of suitable target progenitor cells to which the present therapeutic compositions should be applied. It is sufficient in such cases to obtain an appropriate stimulatory composition (e.g. a NELL-1 polypeptide), as disclosed herein, and contact the site of the bone fracture or defect with the composition. The nature of this biological environment is such that the appropriate cells will become activated in the absence of any further targeting or cellular identification by the practitioner.

A) Transformation of Cells to Increase NELL-1 Production.

In a more preferred embodiment, the NELL-1 expressing nucleic acids (e.g., cDNA(s)) are cloned into gene therapy vectors that are competent to transfect cells (such as human or other mammalian cells) in vitro and/or in vivo.

Several approaches for introducing nucleic acids into cells in vivo, ex vivo and in vitro have been used. These include lipid or liposome based gene delivery (WO 96/18372; WO 93/24640; Mannino and Gould-Fogerite (1988) *BioTechniques* 6(7): 682-691; Rose U.S. Pat. No. 5,279,833; WO 91/06309; and Felgner et al. (1987) *Proc. Natl. Acad. Sci. USA* 84: 7413-7414) and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4: 43, and Cornetta et al. (1991) *Hum. Gene Ther.* 2: 215).

For a review of gene therapy procedures, see, e.g., Anderson, *Science* (1992) 256: 808-813; Nabel and Felgner (1993) *TIBTECH* 11: 211-217; Mitani and Caskey (1993) *TIBTECH* 11: 162-166; Mulligan (1993) *Science*, 926-932; Dillon (1993) *TIBTECH* 11: 167-175; Miller (1992) *Nature* 357: 455-460; Van Brunt (1988) *Biotechnology* 6(10): 1149-1154; Vigne (1995) Restorative Neurology and Neuroscience 8: 35-36; Kremer and Perricaudet (1995) *British Medical Bulletin* 51(1) 31-44; Haddada et al. (1995) in *Current Topics in Microbiology and Immunology*, Doerfler and Böhm (eds) Springer-Verlag, Heidelberg Germany; and Yu et al., (1994) *Gene Therapy*, 1:13-26.

Widely used retroviral vectors include those based upon murine leukemia virus (MuLV), gibbon ape leukemia virus (GaLV), Simian Immuno deficiency virus (SIV), human immuno deficiency virus (HIV), and combinations thereof See, e.g., Buchscher et al. (1992) *J. Virol.* 66(5) 2731-2739; Johann et al. (1992) *J. Virol.* 66 (5):1635-1640 (1992); Sommerfelt et al., (1990) *Virol.* 176:58-59; Wilson et al. (1989) *J. Virol.* 63:2374-2378; Miller et al., *J. Virol.* 65:2220-2224 (1991); Wong-Staal et al., PCT/US94/05700, and Rosenburg and Fauci (1993) in *Fundamental Immunology*, Third Edition Paul (ed) Raven Press, Ltd., New York and the references therein, and Yu et al., Gene Therapy (1994) supra). The vectors are optionally pseudotyped to extend the host range of the vector to cells which are not infected by the retrovirus corresponding to the vector. The vesicular stomatitis virus envelope glycoprotein (VSV-G) has been used to construct VSV-G-pseudotyped HIV vectors which can infect hematopoietic stem cells (Naldini et al. (1996) *Science* 272:263, and Akkina et al. (1996) *J. Virol.* 70:2581).

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) *Virology* 160:38-47; Carter et al. (1989) U.S. Pat. No. 4,797,368; Carter et al. WO 93/24641 (1993); Kotin (1994) *Human Gene Therapy* 5:793-801; Muzyczka (1994) *J. Clin. Invest.* 94:1351 for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251-3260; Tratschin, et al. (1984) *Mol. Cell. Biol.*, 4: 2072-2081; Hermonat and Muzyczka (1984) *Proc. Natl. Acad. Sci. USA*, 81: 6466-6470; McLaughlin et al. (1988) and Samulski et al. (1989) *J. Virol.*, 63:03822-3828. Cell lines that can be transformed by rAAV include those described in Lebkowski et al. (1988) *Mol. Cell. Biol.*, 8:3988-3996. Other suitable viral vectors include herpes virus and vaccinia virus.

U.S. Pat. Nos. 5,942,496 and 5,763,416 disclose methods, compositions, kits and devices for use in transferring nucleic acids into bone cells in situ and/or for stimulating bone progenitor cells (see also, Evans and Robbins (1995) *J. Bone and Joint Surgery*, 77-A(7): 1103-1114, Wolff et al. (1992) *J. Cell Sci.*, 103:1249-1259).

B) Administration of Exogenously Produced NELL-1.

1) Delivery of NELL-1 Proteins to Target Cells.

The NELL-1 proteins (or biologically active fragments thereof) of this invention are useful for intravenous, parenteral, topical, oral, or local administration (e.g., by aerosol or transdermally). Particularly preferred modes of administration include intra-arterial injection, injection into fracture sites or delivery in a biodegradable matrix. The NELL-1 proteins agents are typically combined with a pharmaceutically acceptable carrier (excipient) to form a pharmacological composition. Pharmaceutically acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a pharmaceutically acceptable carrier, including a physiologically acceptable compound depends, for example, on the rout of administration of the anti-mitotic agent and on the particular physio-chemical characteristics of the anti-mitotic agent. Preferred formulations for the delivery of bone morphogenic proteins (BMPs) are described in detail in U.S. Pat. No. 5,385,887.

The pharmaceutical compositions can be administered in a variety of unit dosage forms depending upon the method of administration. For example, unit dosage forms suitable for oral administration include powder, tablets, pills, capsules and lozenges. It is recognized that the NELL-1 protein(s), if administered orally, must be protected from digestion. This is typically accomplished either by complexing the protein with a composition to render it resistant to acidic and enzymatic hydrolysis or by packaging the protein in an appropriately resistant carrier such as a liposome. Means of protecting compounds from digestion are well known in the art (see, e.g., U.S. Pat. No. 5,391,377 describing lipid compositions for oral delivery of therapeutic agents).

The pharmaceutical composition of this invention are particularly useful for topical administration e.g., in surgical wounds to treat facilitate bone reconstruction and/or repair. In another embodiment, the compositions are useful for parenteral administration, such as intravenous administration or administration into a body cavity or lumen of an organ. The compositions for administration will commonly comprise a solution of the NELL-1 protein dissolved in a pharmaceutically acceptable carrier, preferably an aqueous carrier for water-soluble proteins. A variety of carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of NELL-1 protein in these formulations can vary widely, and will be selected primarily based on fluid volumes, viscosities, body weight and the like in accordance with the particular mode of administration selected and the patient's needs. Typically the NELL-1 proteins are utilized in the form of a pharmaceutically acceptable solution (including reconstitution from a lyophilized form). It is optimal to solubilize the osteogenic protein at concentrations of at least about 1 mg/ml, preferably about 2 to 8 mg/ml, so that a pharmaceutically effective amount of protein can be delivered without undue volumes of carrier being necessary. For some applications, concentrations above 2 mg/ml may be desirable.

As alluded to above, the dosage regimen will be determined by the clinical indication being addressed, as well as by various patient variables (e.g. weight, age, sex) and clinical presentation (e.g. extent of injury, site of injury, etc.). In general, the dosage of osteogenic protein will be in the range of from 1 to about 10000 μg, preferably from about about 10 to 1000 μg, more preferably from about 10 to 100 μg.

2) Bone Graft Materials.

Bone wounds, as well as many other wound models, initiate a release of biologically active agents critical to the wound healing process. Bone morphogenic proteins (BMP), which naturally occur in bone, once released from the wound, stimulate osteoinduction and regenerate lost or damaged bone tissue. These same proteins, in a purified form, can be used to stimulate bone growth into a biodegradable matrix allowing for artificial creation of bone both within and external to the normal skeletal boundaries. Without being bound to a particular theory, it is believed that NELL-1 proteins can be used to stimulate bone re-mineralization in a manner analogous to the use of bone morphogenic proteins.

NELL-1 proteins can be administered systemically as discussed above. In addition, or alternatively, the NELL-1 protein can be applied directly to a bone or bone fracture site. This can be accomplished during surgery (e.g. when setting complex fractures, when reconstructing bone, when performing bone transplants, etc.) or can be accomplished by direct injection.

In certain preferred embodiments, particularly where bone reconstruction or repair is performed surgically, it is desired to administer the NELL-1 protein using a sustained delivery "vehicle". Sustained delivery vehicles include, but are not limited to biodegradable delivery vehicles. Preferred biodegradable delivery vehicles are preferably porous.

Much work has been done in developing biodegradable porous delivery vehicles for the controlled release of substances while also providing a location for cellular attachment and guided tissue regeneration. Biodegradable materials often separated into two categories: 1) those which are hydrophilic; and 2) those which are hydrophobic. Hydrophilic materials (demineralized freeze dried bone, ceramic, fibrin, gelatin, etc.) possess a high affinity for water which provides for easy incorporation of aqueous NELL-1 protein solutions within the internal porosity of the material. Hydrophobic materials (L-polylactic acid, D,L-polylactic acid, poly-glycolic acid, etc.), while potentially limitless in their range of porosities, gross size, shape and mechanical characteristics are more difficult to "infiltrate" with aqueous solutions. To increase deposition of solutions into internal surfaces of such materials, hydrophobic materials are often impregnated with the protein or a surfactant is used to facilitate impregnation with the protein (e.g. NELL-1).

Detailed descriptions of various biodegradable delivery materials comprising materials such as fibrinogen, polylactic acid, porous ceramics, gelatin, agar, and the like, can be found, e.g., in U.S. Pat. Nos. 5,736,160, 4,181,983, 4,186,448, 3,902,497, 4,442,655, 4,563,489, 4,596,574, 4,609,551, 4,620,327, and 5,041,138.

Other delivery vehicles include, but are not limited to bone graft materials. Bone graft materials can be derived from natural materials (e.g. transplanted bone or bone fragments), synthetic materials (e.g. various polymers and/or ceramics) or combinations of both. Bone graft materials are typically utilized to fill voids or otherwise replace lost bone material. Such graft materials are also often provided as components of prosthetic devices (e.g., bone replacements or supports) to facilitate tight bonding/annealing of the prosthetic with the living bone.

Bone grafts using bioactive glasses and calcium phosphates, collagen, mixtures and the like have good biocompatibility and give rise to bone tissue formation and incorporation in some cases. A number of different glasses, glass-ceramics, and crystalline phase materials have been used, either alone or in combination with acrylic polymerizable species, and other families of polymers, for restorative purposes. These include hydroxyapatite, fluorapatite, oxyapatite, Wollastonite, anorthite, calcium fluoride, agrellite, devitrite, canasite, phlogopite, monetite, brushite, octocalcium phosphate, Whitlockite, tetracalcium phosphate, cordierite, and Berlinite. Representative patents describing such uses include U.S. Pat. Nos. 3,981,736, 4,652,534, 4,643,982, 4,775,646, 5,236,458, 2,920,971, 5,336,642, and 2,920,971. Additional references include Japanese Patent No. 87-010939 and German Patent OS 2,208,236. Other references may be found in W. F. Brown, "Solubilities of Phosphate & Other Sparingly Soluble Compounds," Environmental Phosphorous Handbook, Ch. 10 (1973). In addition to the foregoing, certain animal derived materials, including coral and nacre, have also been used in biomaterials for restorative purposes.

Other bone graft materials include a pliable, moldable acrylic-based bone cement reinforced with from 15 to 75% by weight of a bioactive glass together with between 1 and 10% by weight of vitreous mineral fibers (U.S. Pat. No. 4,239,113), bone fillers such as tricalcium phosphate and bioceramic $A_2$ into bisphenol-A-diglycidyl methacrylate (bis GMA) polymerizable through the action of peroxide systems such as benzoyl peroxide mixed with amines, (Vuillemin et al. (1987) *Arch. Otolygol. Head Neck Surg.* 113: 836-840). Two component, resin composites containing both salicylates and acrylates, cured through a calcium hydroxide cement reaction are described in U.S. Pat. No. 4,886,843, while U.S. Pat. Nos. 5,145,520 and 5,238,491, discloses fillers and cements. The foregoing materials can be fabricated so as to incorporate NELL-1 proteins.

In addition, graft materials that include bone morphogenic proteins are known. Thus, for example, U.S. Pat. No. 4,394,370 describes complexes of reconstituted collagen and demineralized bone particles or reconstituted collagen and a solubilized bone morphogenetic protein fabricated in a sponge suitable for in vivo implantation in osseous defects are disclosed. Similarly U.S. Pat. No. 5,824,084 describes substrates made from a biocompatible, implantable graft material, preferably having a charged surface. Examples of biocompatible, implantable graft materials include synthetic ceramics comprising calcium phosphate, some polymers, demineralized bone matrix, or mineralized bone matrix. These materials may additionally contain cell adhesion molecules bound to the surface of the substrate. The term "cell adhesion molecules" refers collectively to laminins, fibronectin, vitronectin, vascular cell adhesion molecules (V-CAM) and intercellular adhesion molecules (I-CAM) and collagen. Particularly suitable graft materials include, for example, isolated mineralized cancellous bone sections, powders or granules of mineralized bone, demineralized cancellous bone sections, powders or granules of demineralized bone, guanidine-HCl extracted demineralized bone matrix, sintered cortical or cancellous bone, coralline hydroxyapatite sold by Interpore under the trade name Interpore 500, and granular ceramics such as that incorporated into the bone graft substitute Collagraft sold by Zimmer, or filamentous sponges such as those made from collagen by Orquest. NELL-1 proteins can be incorporated into any of these graft materials or substituted in place of the bone morphogenic protein.

VII. Kits.

In still another embodiment, this invention provides kits for practice of the assays or use of the compositions described herein. In one preferred embodiment, the kits comprise one or more containers containing antibodies and/or nucleic acid probes and/or substrates suitable for detection of NELL-1 expression and/or activity levels. The kits may optionally include any reagents and/or apparatus to facilitate practice of the assays described herein. Such reagents include, but are not limited to buffers, labels, labeled antibodies, labeled nucleic acids, filter sets for visualization of fluorescent labels, blotting membranes, and the like.

In another embodiment, the kits can comprise a container containing a NELL-1 protein, or a vector encoding a NELL-1 protein and/or a cell comprising a vector encoding a NELL-1 protein.

In addition, the kits may include instructional materials containing directions (i.e., protocols) for the practice of the assay methods of this invention or the administration of the compositions described here along with counterindications. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

NELL-1 Enhances Mineralization in Fetal Calvarial Osteoblastic Cells

The nucleotide sequence of the full length cDNA of the NELL-1 gene described herein has approximately 61% homology to the chicken Nel gene, and therefore, was named human NELL-1 (Watanabe et al. (1996) *Genomics.* 38(3), 273-276). NELL-1 proteins contain a signal peptide, a $NH_2$- terminal thrombospondin (TSP)-like module (François and Bier (1995) *Cell.* 80(1):19-20), five von Willebrand factor C domains, and six EGF-like domains.

The human NELL-1 gene expressions were primarily localized in the mesenchymal and osteoblast cells at the osteogenic front, along the parasutural bone margins, and within the condensing mesenchymal cells of newly formed bone. A human multiple-organ tissue mRNA blot showed that human NELL-1 was specifically expressed in fetal brain but not in fetal lung, kidney or liver. We also demonstrated that NELL-1 was expressed in rat calvarial osteoprogenitor cells but was largely absent in rat tibia, stromal cell, and fibroblast cell culture. Our data suggest that the NELL-1 gene is preferentially expressed in cranial intramembranous bone and neural tissue (neural crest origin).

A) Materials and Methods

Whole mouse embryo RNA analysis from the fetal gestation day 7, 11, 14, 17, was performed. Adenoviruses (AD5 with an E1-A knock-out and MCV promoter) carrying NELL-1 cDNA were constructed and infected into rat fetal calvarial primary cell cultures and MC3T3 cell lines. Viruses were constructed according the following protocol: the 293 cells were co-transfected with 10 mg each of pJM17 (containing defective adenovirus genome) and pAC-CMV-based plasmid (containing sense or antisense rat NELL-1 using $CaPO_4$) to produce recombinant adenovirus vectors expressing rat NELL-1 in 10-14 days. Viruses were plaque-purified and Southern blots were performed to assure the incorporation of the NELL-1 gene. Adenoviruses containing the β-Galactosidase gene were used as a control and examined for the efficacy of infection with different cell types. Approximately 80-90% infection efficiency was observed in both MC3T3 and NIH3T3 cells.

Von Kossa staining was performed on 14, 17, 21 day post-infections. Area of mineralization was quantitated by ImagePro system. Statistical analysis was performed by two-tailed Student's t test. A statistical P value of $*p<0.01$ was considered significant. RNA from cells over-expressing NELL-1 was extracted and mouse cDNA array analysis was performed. Hybridization signals were quantitated by phosphoimager.

B) Results

NELL-1 mRNA was faintly expressed from day 14 of gestation with mild increase over the gestation period. Day 14 gestation is the time point when fetal calvaria starts to mineralize. Both primary rat fetal calvarial cell cultures and MC3T3 cell cultures over-expressing NELL-1 showed an increase in mineralization over the β-Galactosidase control. Over-expression of NELL-1 enhanced mineralization in calvarial osteogenic primary cell cultures by approximately 30 folds on day 17 post-infection compared to the control. These results were based on Von Kossa staining and quantitated by ImagePro software. This relative increase decreased to 2 fold by day 21 post infection. Mouse cDNA array results from NELL-1 infected MC3T3 cells showed 20% down regulation in BMP-7 gene expression and a three fold up regulation of the Split Hand and Foot gene compared to the control. These two genes are closed related to bone formation and craniofacial development.

C) Discussions and Conclusions

In this study, we clearly confirmed that NELL-1 is closely associated with bone formation and it enhanced mineralization of the calvarial osteoblast-like cells. Some of the down stream effectors identified clearly play important roles in bone formation and embryological development. Premature cranial suture closure, as seen in CS, may be due to overproduction of cranial bone, and therefore, possibly be associated with the over-expression of the NELL-1 molecule. These results and the preliminary protein function analysis results of the NELL-1 classify this protein as a biologically relevant molecule. As a possible role of NELL-1, these proteins may act as a modulator, interacting with other growth factors. Recently, TSP-1 was shown to be a major activator of TGFβ-1 (François and Bier (1995) *Cell.* 80(1):19-20). TGFβ-1 is secreted by most cells in an inactive form that is unable to interact with cellular receptors. The activity of TGFβ-1 is initially masked by its noncovalent association with a dimer of its $NH_2$-terminal propeptide, called latency-associated protein (LAP). In activating TGFβ-1 extracellularly, TSP-1 interacts with the $NH_2$-terminal region of LAP, forming a trimolecular complex. Within the complex, a conformational change takes place that makes TGFβ-1 accessible to the receptor. Molecules with high homology like chordin, which possess four vWF C domains (presumably homotrimer), is secreted during gastrulation and plays a pivotal role in the *Xenopus* dorsoventral patterning (Crawford et al. (1998) *Cell.* 93(7):1159-1170). Recently, chordin was revealed to directly bind to ventral BMP-4 (bone morphogenetic proteins 4, one of the TGFβ superfamily) and neutralize the BMP-4 activity (Piccolo et al. (1996) *Cell,* 86(4):589-598). These results suggest that NELL-1 protein may execute their unidentified functions extracellularly by interacting with some of the TGFβ superfamily members. Since TGFβ-1 is known as a regulator of osteogenesis, NELL-1's effect in enhancing mineralization may be related to its interaction with the TGFβ superfamily.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A bone graft material capable of enhancing the formation of osseous tissue in the animal in which it is implanted comprising a biocompatible matrix and a NELL-1 protein in an amount effective for stimulating a progenitor cell such that it is activated to differentiate into an osteoblast wherein the NELL-1 protein is selected from NELL-1 proteins encoded by SEQ ID NO. 1 and SEQ ID NO.2.

2. The bone graft material of 1, wherein the biocompatible matrix is resorbable.

3. The bone graft material of claim 1, wherein the biocompatible matrix comprises a resorbable polymer.

4. The bone graft material of claim 1, wherein the NELL-1 protein is produced by a cell within the matrix expressing exogenous NELL-1 protein.

5. The bone graft material of claim 1, wherein the biocompatible matrix comprises a cell adhesion molecule.

6. The bone graft material of claim 1, wherein the biocompatible matrix comprises a bioglass.

7. The bone graft material of claim 1, wherein the biocompatible matrix comprises a bioceramics.

8. The bone graft material of claim 1, wherein the biocompatible matrix comprises a collagen.

9. The bone graft material of claim 1, wherein the biocompatible matrix comprises a collagen in an amount ranging from about 65 to about 95 weight percent of the total bone graft material.

10. The bone graft material of claim 1, further comprising a bone morphogenic protein.

* * * * *

SEQUENCE LISTING

<160> NUMBER OF SEQ ID NOS: 2

<210> SEQ ID NO 1
<211> LENGTH: 2977
<212> TYPE: DNA
<213> ORGANISM: Homo sapiens

```
<400> SEQUENCE: 1
tagcaagttt ggcggctcca agccaggcgc gcctcaggat ccaggctcat tgcttccac      60 ctagcttcgg tgcccctgc taggcgggga ccctcgagag cgatgccgat ggatttgatt     120
ttagttgtgt ggttctgtgt gtgcactgcc aggacagtgg tgggctttgg gatggaccct    180
gaccttcaga tggatatcgt caccgagctt gaccttgtga acaccaccct tggagttgct    240
caggtgtctg gaatgcacaa tgccagcaaa gcatttttat ttcaagacat agaaagagag    300
atccatgcag ctcctcatgt gagtgagaaa ttaattcagc tgttccagaa caagagtgaa    360
ttcaccattt tggccactgt acagcagaag ccatccactt caggagtgat actgtccatt    420
cgagaactgg agcacagcta ttttgaactg gagagcagtg gcctgaggga tgagattcgg    480
tatcactaca tacacaatgg gaagccaagg acagaggcac ttccttaccg catggcagat    540
ggacaatggc acaaggttgc actgtcagtt agcgcctctc atctcctgct ccatgtcgac    600
tgtaacagga tttatgagcg tgtgatagac cctccagata caaccttcc cccaggaatc    660 aatttatggc ttggccagcg caaccaaaag catggcttat tcaaagggat catccaagat    720
gggaagatca tctttatgcc gaatggatat ataacacagt gtccaaatct aaatcacact    780
tgcccaacct gcagtgattt cttaagcctg gtgcaaggaa taatggattt acaagagctt    840
ttggccaaga tgactgcaaa actaaattat gcagagacaa gacttagtca attggaaaac    900
tgtcattgtg agaagacttg tcaagtgagt ggactgctct atcgagatca agactcttgg    960
gtagatggtg accattgcag gaactgcact tgcaaaagtg gtgccgtgga atgccgaagg   1020
atgtcctgtc cccctctcaa ttgctcccca gactccctcc cagtacacat tgctggccag   1080
tgctgtaagg tctgccgacc aaaatgtatc tatgaggaa aagttcttgc agaaggccag   1140
cggattttaa ccaagagctg tcgggaatgc cgaggtggag ttttagtaaa aattacagaa   1200
atgtgtcctc ctttgaactg ctcagaaaag gatcacattc ttcctgagaa tcagtgctgc   1260
cgtgtctgta gaggtcataa cttttgtgca gaaggaccta aatgtggtga aaactcagag   1320
tgcaaaaact ggaatacaaa agctacttgt gagtgcaaga gtggttacat ctctgtccag   1380
ggagactctg cctactgtga agatattgat gagtgtgcag ctaagatgca ttactgtcat   1440
gccaatactg tgtgtgtcaa ccttcctggg ttatatcgct gtgactgtgt cccaggatac   1500
attcgtgtgg atgacttctc ttgtacagaa cacgatgaat gtggcagcgg ccagcacaac   1560
tgtgatgaga atgccatctg caccaacact gtccagggac acagctgcac ctgcaaaccg   1620
ggctacgtgg ggaacgggac catctgcaga gctttctgtg aagagggctg cagatacggt   1680
ggaacgtgtg tggctcccaa caaatgtgtc tgtccatctg gattcacagg aagccactgc   1740
gagaaagata ttgatgaatg ttcagaggga atcattgagt gccacaacca ttccgctgc    1800 gttaacctgc cagggtggta ccactgtgag tgcagaagcg gtttccatga cgatgggacc   1860
tattcactgt ccggggagtc ctgtattgac attgatgaat gtgccttaag aactcacacc   1920
tgttggaacg attctgcctg catcaacctg gcagggggtt ttgactgtct ctgcccctct   1980
gggccctcct gctctggtga ctgtcctcat gaagggggggc tgaagcacaa tggccaggtg   2040
tggaccttga agaagacag tgttctgtc tgctcctgca aggatggcaa gatattctgc    2100
cgacggacag cttgtgattg ccagaatcca agtgctgacc tattctgttg cccagaatgt   2160
gacaccagag tcacaagtca atgtttagac caaaatggtc acaagctgta tcgaagtgga   2220
gacaattgga cccatagctg tcagcagtgt cggtgtctgg aaggagaggt agattgctgg   2280
```

| | |
|---|---:|
| ccactcactt gccccaactt gagctgtgag tatacagcta tcttagaagg ggaatgttgt | 2340 |
| ccccgctgtg tcagtgaccc ctgcctagct gataacatca cctatgacat cagaaaaact | 2400 |
| tgcctggaca gctatggtgt ttcacggctt agtggctcag tgtggacgat ggctggatct | 2460 |
| ccctgcacaa cctgtaaatg caagaatgga agagtctgtt gttctgtgga ttttgagtgt | 2520 |
| cttcaaaata attgaagtat ttacagtgga ctcaacgcag aagaatggac gaaatgacca | 2580 |
| tccaacgtga ttaaggatag gaatcggtag tttggttttt tgtttgttt tgttttttta | 2640 |
| accacagata attgccaaag tttccacctg aggacggtgt tcggaggtt gccttttgga | 2700 |
| cctaccactt tgctcattct tgctaaccta gtctaggtga cctacagtgc cgtgcattta | 2760 |
| agtcaatggt tgttaaaaga agtttcccgt gttgtaaatc atgtttccct tatcagatca | 2820 |
| tttgcaaata catttaaatg atctcatggt aaatggttga tgtatttttt gggtttattt | 2880 |
| tgtgtactaa ccataataga gagagactca gctccttta tttattttgt tgatttatgg | 2940 |
| atcaaattct aaaataaagt tgcctgttgt gactttt | 2977 |

<210> SEQ ID NO 2
<211> LENGTH: 1722
<212> TYPE: DNA
<213> ORGANISM: Homo sapiens
<220> FEATURE:
<221> NAME/KEY: misc_feature
<223> OTHER INFORMATION: n is a, c, g, or t

<400> SEQUENCE: 2

| | |
|---|---:|
| gatcagtgct gccgtgtctg tagaggtcat aactttttgtg cagaaggacc taaatgtggt | 60 |
| gaaaactcag agtgcaaaaa ctggaataca aaagctactt gtgagtgcaa gagtggttac | 120 |
| atctctgtcc aggggagact ctgcctactg tgaagatatt gatgagtgtg cagctaagat | 180 |
| gcattactgt catgccaata ctgtgtgtgt caaccttcct gggttatatc gctgtgactg | 240 |
| tgtcccagga tacattcgtg tggatgactt ctcttgtaca gaacacgatg aatgtggcag | 300 |
| cggccagcac aactgtgatg agaatgccat ctgcaccaac actgtccagg acacagctg | 360 |
| cacctgcaaa ccgggctacg tggggaacgg gaccatctgc agagctttct gtgaagaggg | 420 |
| ctgcagatac ggtggaacgt gtgtggctcc caacaaatgt gtctgtccat ctggattcac | 480 |
| aggaagccac tgcgagaaag atattgatga atgttcagag ggaatcattg agtgccacaa | 540 |
| ccattcccgc tgcgttaacc tgccagggtg gcaccactgt gagtgcagaa gcggtttcca | 600 |
| tgacgatggg acctattcac tgtccgggga gtcctgtatt gacattgatg aatgtgcctt | 660 |
| aagaactcac acctgttgga acgattctgc ctgcatcaac ctggcagggg gttttgactg | 720 |
| tctctgcccc tgtgggccct cctgctctgg tgactgtcct catgaagggg ggctgaagca | 780 |
| caatggccag gtgtggacct tgaaagaaga caggtgttct gtctgctcct gcaaggatgg | 840 |
| taagatattc tgccgacgga cagcttgtga ttgccagaat ccaagtgctg acctattctg | 900 |
| ttgcccagaa tgtgacacca gagtcacaag tcaatgttta gaccaaaatg gtcacaagct | 960 |
| gtatcgaagt ggagacaatt ggacccctag ctgtcagcag tgtcggtgtc tggaaggaga | 1020 |
| ggtagattgc tggccactca cttgccccaa cttgagctgt gagtatacag ctatcttaga | 1080 |
| aggggaatgt tgtccccgct gtgtcagtga ccccctgccta gctgataaca tcacctatga | 1140 |
| catcagaaaa acttgcctgg acagtatggt gtttcacggc ttagtggctc agtgtggacg | 1200 |
| atggctggat ctccctgcac aacctgtaaa tgcaagaatg aaagagtctg ttgttctgtg | 1260 |
| gattttgagt gtcttcaaaa taattgaagt atttacagtg gactcaacgc agaagaatgg | 1320 |

```
acgaaatgac catccaacgt gattaaggat aggaatcggt agtttggttt ttttgtttgt    1380
tttgtttttt taaccacaga taattgccaa agtttccacc tgaggacggt gtttggaggt    1440
tgccttttgg acctaccact ttgctcattc ttgctaacct agtttaggtg acctacagtg    1500
ccgtgcattt aagtcagtgg ttgttaaaag aagtttcccg cgttgtaaat catgtttccc    1560
ttatcagatc atttgcaaat acatttaaat gatntcatgg taaatgttgc tgtattttt     1620 ggtttatttt ctgtactaac ataatagaga gagantnagc tccttttatt tattttgttg    1680
atttatggat caaattntaa aataaagttg cctgttgtgn aa                       1722
```